(12) United States Patent
Gallagher

(10) Patent No.: US 7,426,442 B2
(45) Date of Patent: *Sep. 16, 2008

(54) SOFTWARE FOR THE DISPLAY OF CHROMATOGRAPHIC SEPARATION DATA

(75) Inventor: Steven J. Gallagher, Palo Alto, CA (US)

(73) Assignee: Caliper Technologies, Corp., Mountain View, CA (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/900,761

(22) Filed: Jul. 27, 2004

(65) Prior Publication Data

US 2005/0010375 A1   Jan. 13, 2005

Related U.S. Application Data

(63) Continuation of application No. 10/443,657, filed on May 22, 2003, now Pat. No. 6,834,240, which is a continuation of application No. 10/155,324, filed on May 24, 2002, now Pat. No. 6,611,768, which is a continuation of application No. 09/223,070, filed on Dec. 29, 1998, now Pat. No. 6,430,512.

(60) Provisional application No. 60/068,980, filed on Dec. 30, 1997.

(51) Int. Cl.
*G01N 31/00* (2006.01)

(52) U.S. Cl. ........................................................ 702/32

(58) Field of Classification Search ................... 96/103; 702/32

See application file for complete search history.

(56) References Cited

U.S. PATENT DOCUMENTS

| | | | | | |
|---|---|---|---|---|---|
| 5,203,992 | A | * | 4/1993 | Drouen | 210/198.2 |
| 5,627,643 | A | * | 5/1997 | Birnbaum et al. | 356/344 |
| 5,858,195 | A | * | 1/1999 | Ramsey | 204/601 |
| 6,048,707 | A | * | 4/2000 | Klock, Jr. | 435/18 |
| 6,143,152 | A | * | 11/2000 | Simpson et al. | 204/451 |

* cited by examiner

*Primary Examiner*—John Barlow
*Assistant Examiner*—Demetrius R. Pretlow
(74) *Attorney, Agent, or Firm*—Donald R. McKenna; Ann C. Petersen

(57) ABSTRACT

Techniques for displaying chromatographic data using a graphical user interface are provided. Chromatographic separation data that is a series of measurements for a sample at a scanning location over time can be displayed on a display device in a series of bands. Additionally, the series of bands for multiple samples can be aligned on the display device.

8 Claims, 18 Drawing Sheets

SOFTWARE FOR THE DISPLAY OF CHROMATOGRAPHIC SEPARATION DATA

This application is a continuation of U.S. application Ser. No. 10/443,657, filed on May 22, 2003, and issued on Dec. 21, 2004, as U.S. Pat. No. 6,834,240, which is a continuation of U.S. application Ser. No. 10/155,324, filed on May 24, 2002, and issued on Aug. 26, 2003, as U.S. Pat. No. 6,611, 768, which is a continuation of U.S. application Ser. No. 09/223,070, filed on Dec. 29, 1998, and issued on Aug. 6, 2002, as U.S. Pat. No. 6,430,512, all of which claim the benefit of U.S. Provisional Application No. 60/068,980, filed on Dec. 30, 1997, which is incorporated herein by reference.

BACKGROUND OF THE INVENTION

The present invention relates to the graphical display of data. More specifically, the invention relates to the display of chromatographic separation data that are a series of measurements over time in a graphical format, e.g., as a series of bands.

Analysis of biological samples often requires the resolution and characterization of the constituent elements of the sample. The more interesting of these constituents are macromolecular structures, e.g., proteins, nucleic acids, carbohydrates, and the like. Typically, analytical separation of macromolecular species is carried out using chromatographic techniques. Of particular widespread use are electrophoretic techniques that employ slab-gels disposed between two glass plates as a separation matrix. Samples containing the macromolecular species that are sought to be analyzed, are introduced into wells at one end of the slab gel. An electric current is then applied through the gel drawing the macromolecular species through the gel by virtue of a charge either on, or otherwise associated with the macromolecular species. Each sample travels through the gel substantially linearly, e.g., in a lane corresponding to its well.

As the sample progresses through the gel, molecules of different size and/or charge will have different mobilities through the gel, and will separate into bands that reflect their relative size and/or charge. Upon completion, the gel is stained or otherwise examined whereby the various bands can be visualized and compared with standard macromolecular compounds, e.g., having standard molecular weight and/or charge, e.g., isolectric point.

For example, in the case of protein analysis using sodium dodecylsulfate polyacrylamide gel electrophoresis (SDS-PAGE), proteins are drawn through the gel matrix in a highly charged detergent micelle (SDS) to ensure that the proteins, regardless of charge, will electrophorese through the gel. The proteins will travel at a rate that is proportional to their size. Once separated, the protein bands are stained, e.g., with coomassie blue or silver staining, to permit analysis and recordation, e.g., as a photograph or a digital or analog scan.

Similarly, nucleic acid analyses utilize a similar gel system, e.g., agarose or polyacrylamide gel. Upon application of a current through the gel, the nucleic acid samples, again disposed in wells at one end (anode) of the gel, will electrophorese through the gel. The polymer gel presents a sieving matrix, where larger nucleic acid fragments that otherwise having the same charge:mass ratio as smaller fragments, will travel more slowly through the gel than the smaller fragments. Upon completion of electrophoresis, the lanes of samples are analyzed for the pattern of the bands (or "ladder" as it is often termed). Analysis of the bands may be carried out by adding a fluorescent intercalating agent to the gel, or by incorporating a radioactive label within the nucleic acid fragments, followed by contacting the gel with a photographic film.

Typically, electrophoresis gels run multiple samples within the same slab gel along with one or more standards or markers, which are used to characterize the sample constituents. For example, in size-based separations, standards typically have a range of known molecular weights. Sample constituents are then compared to the standards to determine their molecular weights, e.g., by interpolation. Such standards must generally be run in the same gel as the sample, in order to provide assurances that the standard was subject to the same separation conditions, e.g., gel composition, electric current, temperature, or other parameters affecting separations.

Despite the efficacy of these slab gel electrophoresis, however, such methods are quickly being supplanted by automated procedures that generate a stream of digital data. This data, in its raw form, may exhibit the non-linearities described earlier, or different ones, or none at all. Such data may be generated, for example, by passing a sample in front of a sensor. Alternatively, it is also possible to digitize the raw information presented in a traditional gel by scanning it to produce a series of measurements. The display of such information is not provided by current systems.

What is therefore needed are techniques for displaying chromatographic separation data that are a series of measurements over time in a format similar to that of traditional gel presentations. Moreover, it would be beneficial to provide normalization of such data, if desired.

SUMMARY OF THE INVENTION

The present invention provides innovative techniques for displaying a series of measurements, e.g., as acquired from a microfluidic capillary separation experiment, in a gel-like format. This gel-like format displays chromatographically separated and detected species as bands of varying width and intensity in a vertical lane format, e.g., as a ladder. This format further permits the side-by-side display of chromatographic data from multiple different samples, which data can be normalized to internal standards. In particular, chromatographic data obtained in the form of optical intensity, e.g., fluorescence, UV absorbance, or the like, as a function of time, e.g., as a chromatogram, can be displayed in a band format, as a ladder. Further, serially acquired data from analysis of multiple samples, e.g., from serial separations in the same separation system, as opposed to parallel acquired data, e.g., from a multi-lane slab gel, can be displayed side-by-side, and can be normalized to one or more standards.

In one embodiment, the invention provides a computer implemented method of displaying chromatographic separation data. A series of measurements indicating presence of constituents in a sample at a scanning location over time is received. The series of measurements for the sample is displayed as a series of bands. Additionally, peaks in the series of measurements can be identified that correspond to one or more markers. The series of measurements can be scaled so that any displayed bands that correspond to the one or more markers are aligned with predetermined locations or markers from a previous or the same sample.

In another embodiment, the invention provides a computer implemented method of displaying chromatographic separation data. A series of measurements indicating the presence of constituents and at least one marker in a first sample at a scanning location over time is received. A series of measurements indicating the presence of constituents and at least one marker in a second sample at a scanning location over time is also received. The series of measurements for the first sample is displayed as a series of bands. The series of measurements for the first sample is analyzed to identify at least one peak that corresponds to the at least one marker. Similarly, the series of measurements for the second sample is analyzed to identify at least one peak that corresponds to the at least one marker. The series of measurements for the second sample are scaled so that the displayed bands that correspond to the at least one marker in the first and second samples are aligned when displayed. Lastly, the series of measurements for the second sample is displayed as a series of bands adjacent to the bands for the first sample.

In another embodiment, the invention provides a computer implemented method of graphically presenting chromatographic separation data. Chromatographic data for a sample is acquired, the chromatographic data for the sample including a set of constituents and a set of markers. A position of each marker in the chromatographic data is determined in order to define a range of positions. Additionally, an intensity of each marker in the chromatographic data is determined in order to define a range of intensities. The position of each constituent in the chromatographic data is determined by scaling the position to the range of positions and the intensity of each constituent in the chromatographic data is determined by scaling the position to the range of range of intensities. The position and intensity of each constituent in the chromatographic data is then presented in a graphical format.

A particularly useful application of these methods and processes is in the field of capillary electrophoresis. In capillary electrophoresis, materials to be separated based upon their size, e.g., nucleic acids, proteins, etc., are introduced into one end of a narrow bore capillary channel, which typically includes a separation matrix, e.g., a polymer solution or gel, disposed therein. Application of an electric field through the capillary channel then draws the sample through the channel. The presence of the polymer solution or gel, or alternatively, differential molecular charges of the macromolecular species, imparts a different mobility to the different macromolecular species in the sample, depending upon their size. Because a single thin channel is used for a given separation, typically only a single sample can be analyzed at any time, but channels could be utilized in parallel. However, a single capillary channel can serially analyze multiple samples effectively and this obviates the need for separately run ranges of standards. Instead, internal standards, e.g., of known molecular weight, typically are included with the sample materials, to provide a reference point against which the sample constituents or components may be compared. Typically, such standards will fall outside of the expected separation range for the sample constituents, e.g., have much larger or smaller molecular weights then the sample constituents. This permits the standards to be readily identified as the standards, and prevents them from interfering with the analysis of the sample constituents. Alternatively, differential labeling techniques may be used, whereby the standards may be distinguished from other constituents of the sample material by virtue of their incorporating a distinguishable label, e.g., having different light absorbing or emitting properties.

Separated species are generally detected at a single point along the length of the capillary channel as they move past that point. Typically, detection is carried out through the incorporation or association of a detectable labeling group with the various macromolecular species. The data from the detector is typically displayed as peaks of optical intensity as a function of time, e.g., as a chromatogram, for each sample analyzed. Analysis of additional samples is then carried out serially, e.g., one after another, in the same capillary system, giving rise to multiple separate plots of optical intensity peaks vs. time. Because these data are obtained from separate runs, with potentially varying conditions, these multiple plots make it very difficult to compare data from different samples.

In one aspect of the present invention, data obtained in the form of a typical chromatographic plot of intensity peaks are displayed as a series of bands of varying widths and intensities, in a vertical ladder-like format. Further, a user may toggle back and forth between the different display modes, e.g., chromatogram and gel-like displays, as well as manipulate of the data to permit optimal comparison and analysis of this data, e.g., normalization of data to standards, interpolation/extrapolation of data to characterize data from the different samples and different constituents of each sample.

A further understanding of the nature and advantages of the invention described herein may be realized by reference to the remaining portions of the specification and the attached drawings.

DETAILED DESCRIPTION OF PREFERRED EMBODIMENTS

Introduction

Figure 1:
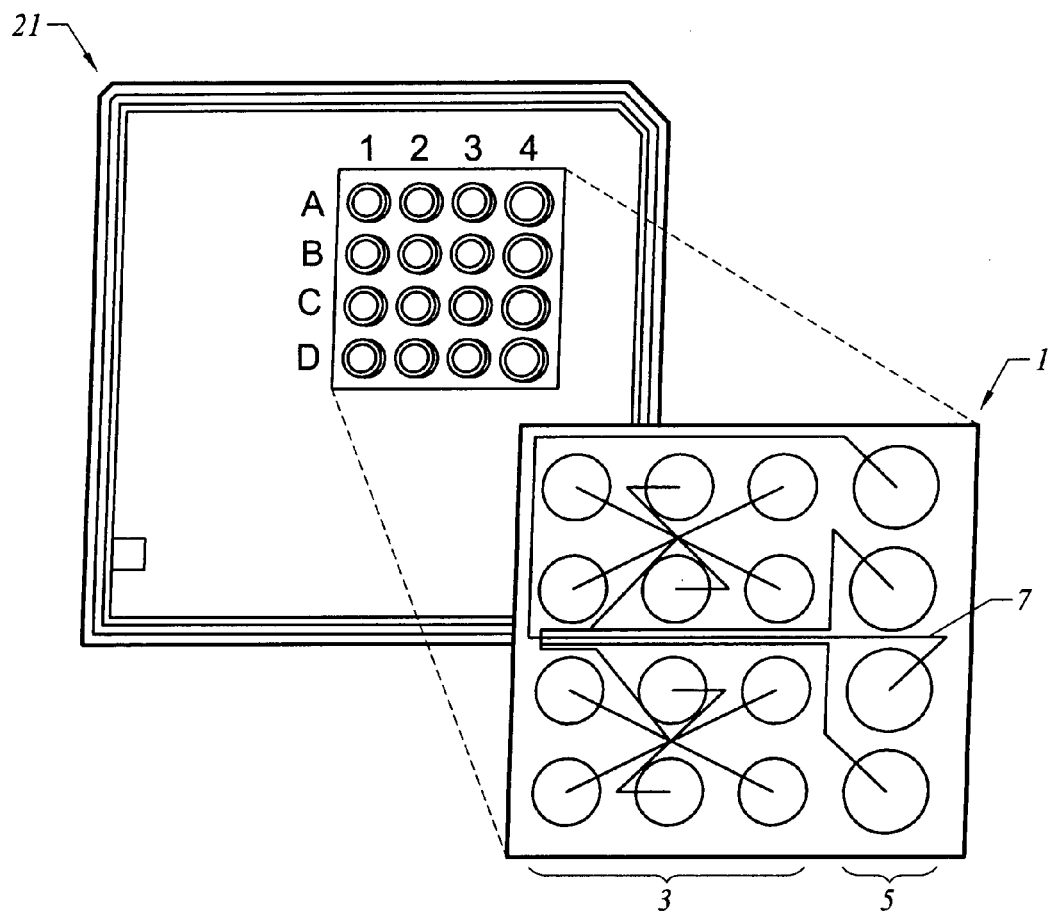
FIG. 1 shows an embodiment of a microfluidic device.

The present invention relates to the display of data from a chemical assay. More particularly, the present invention provides techniques for displaying microfluidic capillary separation data in a "gel" format on the display device of a computer. First, the data generated by the experiment is loaded into the computer. This data can include, among other information, data representing fluorescence levels observed in the sample being analyzed typically as a function of retention time in an electrophoretic separation system, e.g. capillary electrophoresis. These fluorescence levels typically represent one or more standards and one or more constituents of samples. The present invention displays the data as a series of bands like a ladder, in a manner substantially similar to a traditional gel.

In one embodiment, the present invention creates a normalization curve using a set of standards (or markers) of known characteristics, e.g., molecular weight. The constituents of the samples are displayed as a series of bands (also called a "ladder"). These bands (i.e., the fluorescence levels) may be displayed as a positive (white bands on a black background), a negative (black bands on a white background), or using one of a variety of color combinations. The fluorescence data may be displayed in normalized and unnormalized formats. The unknown sample ladder(s) are normalized to the standard ladder by matching the standards embedded in each sample ladder to those of the standard ladder.

One aspect of the present invention is the conversion of serially generated data into a more conventional parallel format. Data generated by systems such as the exemplary system described herein are in a serial format, and would normally be expected to be displayed as such. However, by converting this information into a gel display, the display of chromatographic data by the present invention is made simpler, less expensive (on a per-run basis), and more repeatable than conventional gel assays.

Graphical Display of Chromatographic Data

As noted above, the techniques described herein are particularly useful in analyzing data from capillary electrophoresis applications. However, it will be appreciated that these methods and processes also are useful in a wide variety of chromatographic separation systems, e.g., conventional column chromatography, HPLC, FPLC, mass spectrometry, scanned slab gel methods, and the like.

As also noted, the methods and processes are useful in capillary electrophoretic systems that serially analyze multiple samples within a single capillary channel. In particularly preferred aspects, a planar microfluidic device that includes multiple sample reservoirs coupled to a single separation channel is used in conjunction with the data analysis and presentation methods and processes described herein. Examples of such systems are described in detail in copending, commonly assigned PCT Publication WO 98/49548, and incorporated herein by reference. In particular, multiple different samples disposed in separate sample wells in the body of the device, are separately injected into a single separation channel within the device, one after another.

Exemplary Microfluidic Devices

In preferred aspects, certain of the devices, methods and systems described herein which are used to produce the chromatographic separation data described herein, employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes.

FIG. 1 shows one embodiment of a microfluidic device that can be used with the invention. A device 1 includes multiple wells that are interconnected with microchannels or fluid conduits. As shown, device 1 includes 16 wells in which four wells are slightly larger than the other nine wells. Sample wells 3 can hold fluid samples and buffer wells 5 can be utilized to hold buffer solutions to aid the microfluidic separation process. For example, in macromolecular separation applications, e.g., nucleic acid and protein separations, the buffer solution can include a polymer that sieves the macromolecular species by size as they are driven through it by means of electrophoresis, similar to using agarose or polyacrylarnide gels. The samples and buffer solutions can include an intercalating dye that becomes more fluorescent upon binding to the macromolecular species. Each sample is electrokinetically moved from its well to a central separating channel 7. A small amount of the sample is injected into and electrophoresed in separating channel 7, where the constituents and markers in the sample separate by size and pass a laser (e.g., red laser at 635 nm) that excites the fluorescent dye bound to the macromolecular species. After excitation, the portion of the sample that has reached a scanning location is scanned to produce a series of measurements of fluorescent intensity vs. time. Although fluorescent labels will be described herein, other types of label including light absorbing labels, radioactive labels, and the like can be utilized with the invention.

Typically, the samples in sample wells 3 are serially driven through separating channel 7. Buffer wells 5 can be utilized to "wash" the separating channel between samples. A graphical representation 21 of the device is shown. The graphical representation can be displayed for a user and includes the wells of the device without the microchannels. The wells are shown with a letter identification for the rows and a number identification for the columns. Accordingly, each well (and the sample or buffer therein) can be identified by a combination of letters and numbers (e.g., "A3").

In general, a microfluidic device can include two intersecting channels or fluid conduits, e.g., interconnected, enclosed chambers, and three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection.

In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves that include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the "Off" mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is substantially within the given dimensions.

In the devices of some embodiments of the present invention, the microscale channels or chambers preferably have at least one cross-sectional dimension are also within the given dimensions. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (see U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in PCT Publication WO 98/46438, and which is incorporated herein by reference in its entirety for all purposes.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipetor, which serially introduces multiple samples into the device for analysis. Examples of such sample introduction systems are described in, e.g., PCT Publications WO 98/00231 and WO 98/00705, each of which is hereby incorporated by reference in its entirety for all purposes.

Instrumentation

The systems described herein generally include microfluidic devices, as described above, in conjunction with additional instrumentation for controlling fluid or material transport and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Figure 2:
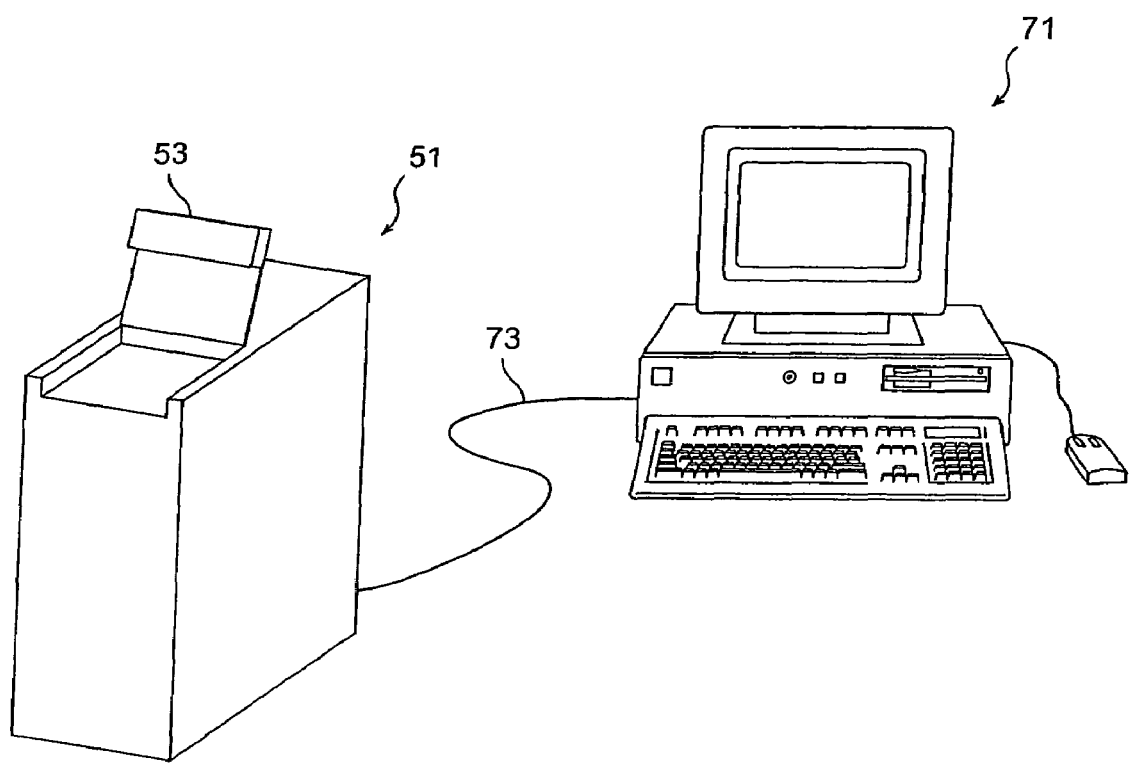
FIG. 2. shows a system including a microfluidic instrument and a computer system.

FIG. 2 shows an embodiment of a microfluidic instrument that can be utilized with the invention. A microfluidic instrument 51 includes a cover 53. The cover overlies a chamber in which a microfluidic device is placed. Preferably, the microfluidic device is configured so that it can only be placed in the correct orientation (e.g., by a notch in one corner of the device). After the microfluidic device is placed in the chamber of microfluidic instrument 51, the user lowers cover 53. In one embodiment, the cover includes multiple electrodes (not shown) that are placed in the wells of the microfluidic device when the cover is lowered. The electrodes are used to drive the fluids through the microchannels of the microfluidic device. In a preferred embodiment, each electrode is separately powered.

Microfluidic instrument 51 is shown electronically connected to a computer system 71 by a cable 73 (e.g., a serial cable). Computer system 71 can be utilized to control microfluidic instrument 51 and analyze the resulting data. Additionally, the electronics to control the microfluidic station can be included in the instrument.

Once chromatographic separation data is obtained, computer system 71 can be utilized to analyze and display the data. Although the computer system is shown connected to the microfluidic instrument directly, the computer system need not be directly connected to the instrument or indeed even at the same location. For example, the computer system can be at a remote site for analysis and receive the chromatographic separation data through a network (e.g., the Internet) or a portable storage medium (e.g., floppy drive). Accordingly, the invention is not limited to the specific configurations shown.

A variety of controlling instrumentation may be utilized in conjunction with the microfluidic devices described above, for controlling the transport and direction of fluids and/or materials within the devices of the present invention. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein preferably utilize electrokinetic material direction and transport systems. As such, the controller systems for use in conjunction with the microfluidic devices typically include an electrical power supply and circuitry for delivering appropriate voltages to a plurality of electrodes that are placed in electrical contact with the fluids contained within the microfluidic devices. Examples of particularly preferred electrical controllers include those described in, e.g., U.S. patent application Ser. No. 08/888,064, and PCT Publication WO 98/00707, the disclosures of which are hereby incorporated herein by reference in their entirety for all purposes. In brief, the controller uses electric current control in the microfluidic system.

The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating undesired temperature effects within the channels.

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. For example, in the present invention, such detectors may include laser fluorescence devices that detect fluorescence induced by exposure to laser radiation to generate the chromatographic data thus displayed. This is a preferred embodiment used in the present invention.

As such, the detection system will typically include collection optics for gathering a light based signal transmitted through the detection window, and transmitting that signal to an appropriate light detector. Microscope objectives of varying power, field diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source that produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broad band light sources are typically used in light scattering/transmissivity detection schemes, and the like. Typically, light selection parameters are well known to those of skill in the art.

The detector may exist as a separate unit, but is preferably integrated with the controller system, into a single instrument. Integration of these functions into a single unit facilitates connection of these instruments with a computer system (described below), by permitting the use of few or a single communication port(s) for transmitting information between the controller, the detector and the computer.

Computer System

As noted above, either or both of the controller system and/or the detection system can be coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

Figure 3:
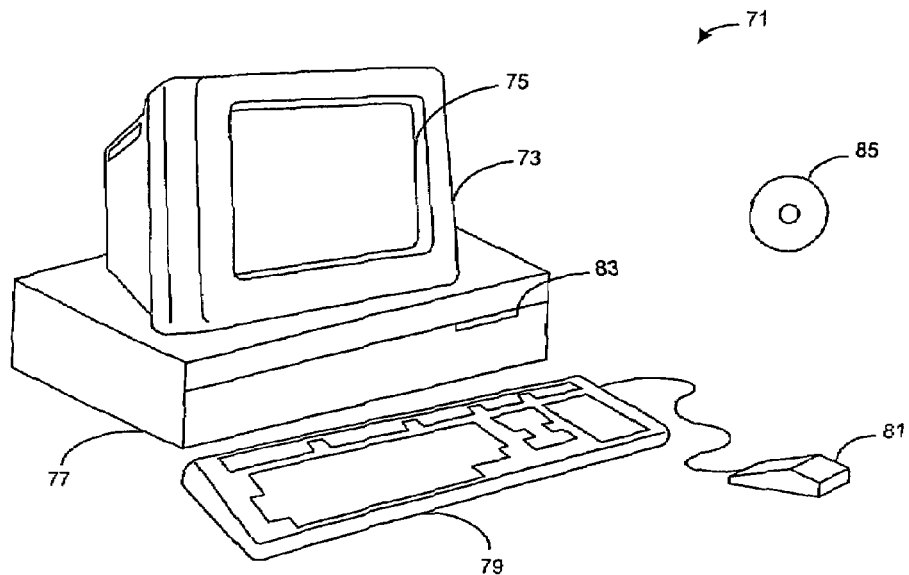
FIG. 3 illustrates an example of a computer system that may be utilized to execute the software of an embodiment of the invention.

FIG. 3 illustrates an example of a computer system that may be used to execute the software of an embodiment of the invention. FIG. 3 shows a computer system 71 that includes a display 73, screen 75, cabinet 77, keyboard 79, and mouse 81. Mouse 81 may have one or more buttons for interacting with a graphical user interface. Cabinet 77 houses a CD-ROM drive 83, system memory and a hard drive (see FIG. 4) which may be utilized to store and retrieve software programs incorporating computer code that implements the invention, data for use with the invention, and the like. Although CD-ROM 85 is shown as an exemplary computer readable storage medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 4:
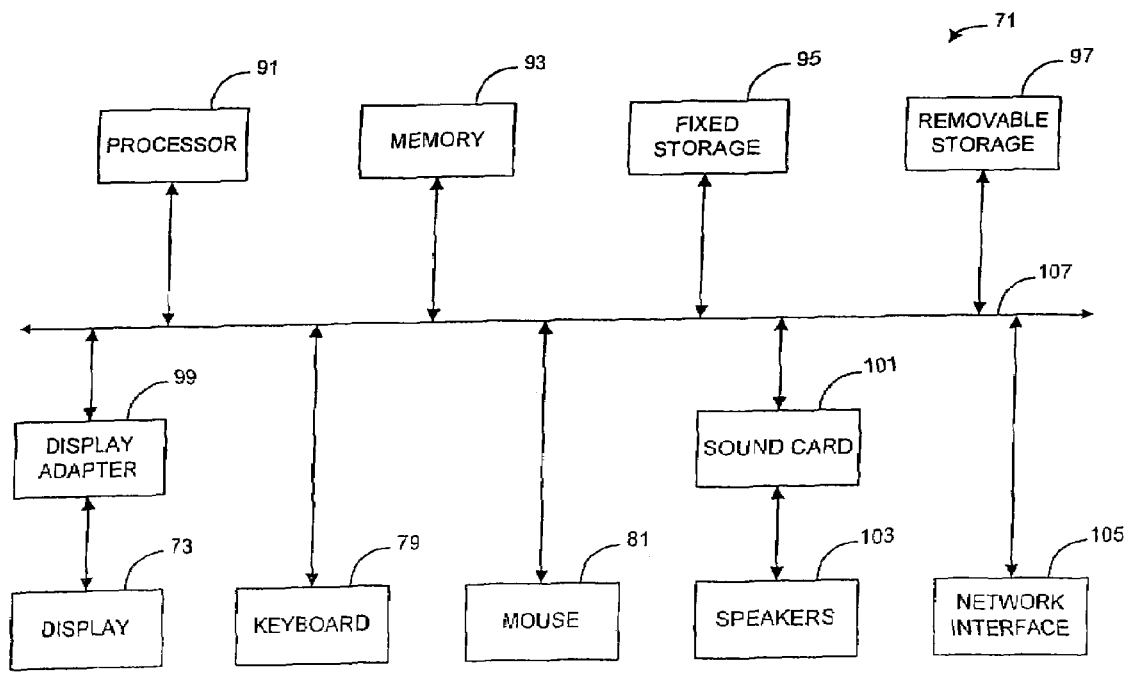
FIG. 4 illustrates a system block diagram of the computer system of FIG. 3.

FIG. 4 shows a system block diagram of computer system 71 used to execute the software of an embodiment of the invention. As in FIG. 3, computer system 71 includes monitor 73 and keyboard 79, and mouse 81. Computer system 71 further includes subsystems such as a central processor 91, system memory 93, fixed storage 95 (e.g., hard drive), removable storage 97 (e.g., CD-ROM drive), display adapter 99, sound card 101, speakers 103, and network interface 105. Other computer systems suitable for use with the invention may include additional or fewer subsystems. For example, another computer system could include more than one processor 91 (i.e., a multi-processor system) or a cache memory.

The system bus architecture of computer system 71 is represented by arrows 107. However, these arrows are illustrative of any interconnection scheme serving to link the subsystems. For example, a local bus could be utilized to connect the central processor to the system memory and display adapter. Computer system 71 shown in FIG. 4 is but an example of a computer system suitable for use with the invention. Other computer architectures having different configurations of subsystems may also be utilized.

The computer system typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like. Thus, a graphical display of chromatographic separation data according to the present invention provides greater flexibility in the display of such data, and features heretofore unseen in the display of such information.

Device Integration

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

Display of Chromatographic Separation Data

The chromatographic separation data can be analyzed on a computer system that is connected to the microfluidic instrument or one that receives the data remotely. The chromatographic separation data typically is in the form of a measured intensity (be it fluorescence or otherwise) at a scanning location vs. time. A graphical plot of intensity vs. time can be very useful, but many scientists and researchers are not accustomed to this format for electrophoresis separation analysis. Further, the side by side comparison of such data from multiple samples can be difficult.

Figure 5:
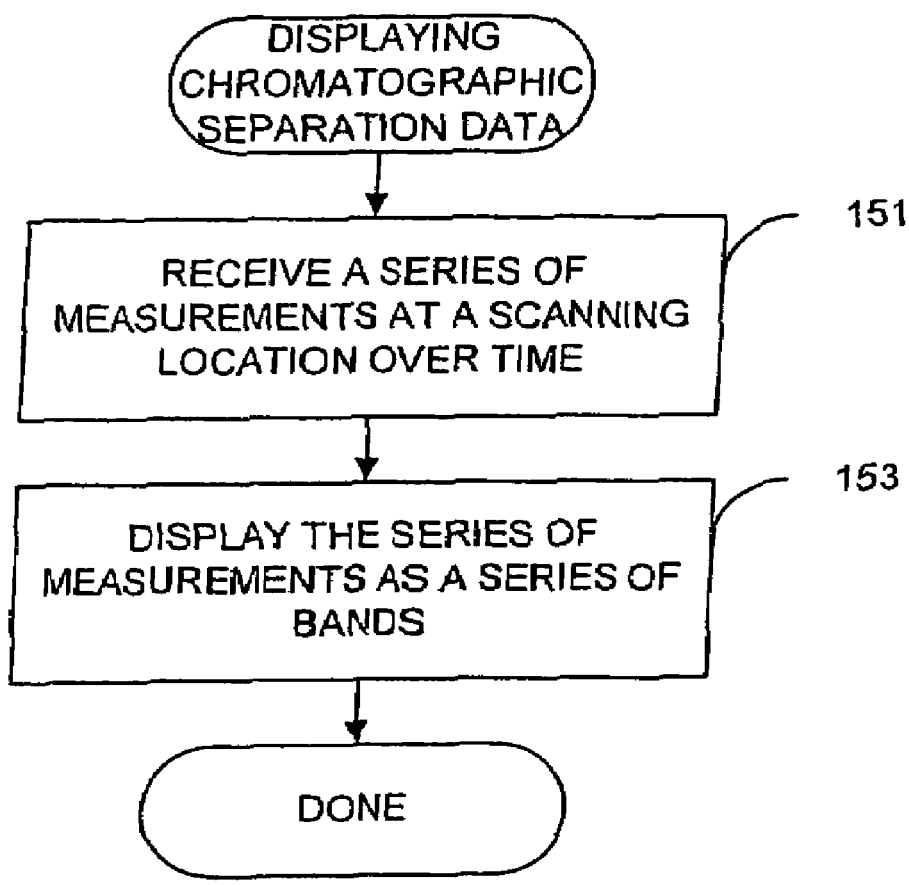
FIG. 5 shows a flowchart of a process of displaying chromatographic separation data that is a series of measurements at a scanning location over time as a series of bands.

FIG. 5 shows a high level flowchart of a process of displaying chromatographic data that is a series of measurements at a scanning location over time as a series of bands. At a step 151, the computer system receives a series of measurements at a scanning location over time. The series of measurements can be fluorescent intensities that were measured at the scanning location of the microfluidic device as a sample was electrokinetically pulled through the separation channel. The computer system displays the series of measurements as a series of bands at a step 153. The series of bands can resemble a conventional electrophoresis gel that users may find more familiar. A graphical plot of intensity vs. time can also be displayed.

Figure 6:
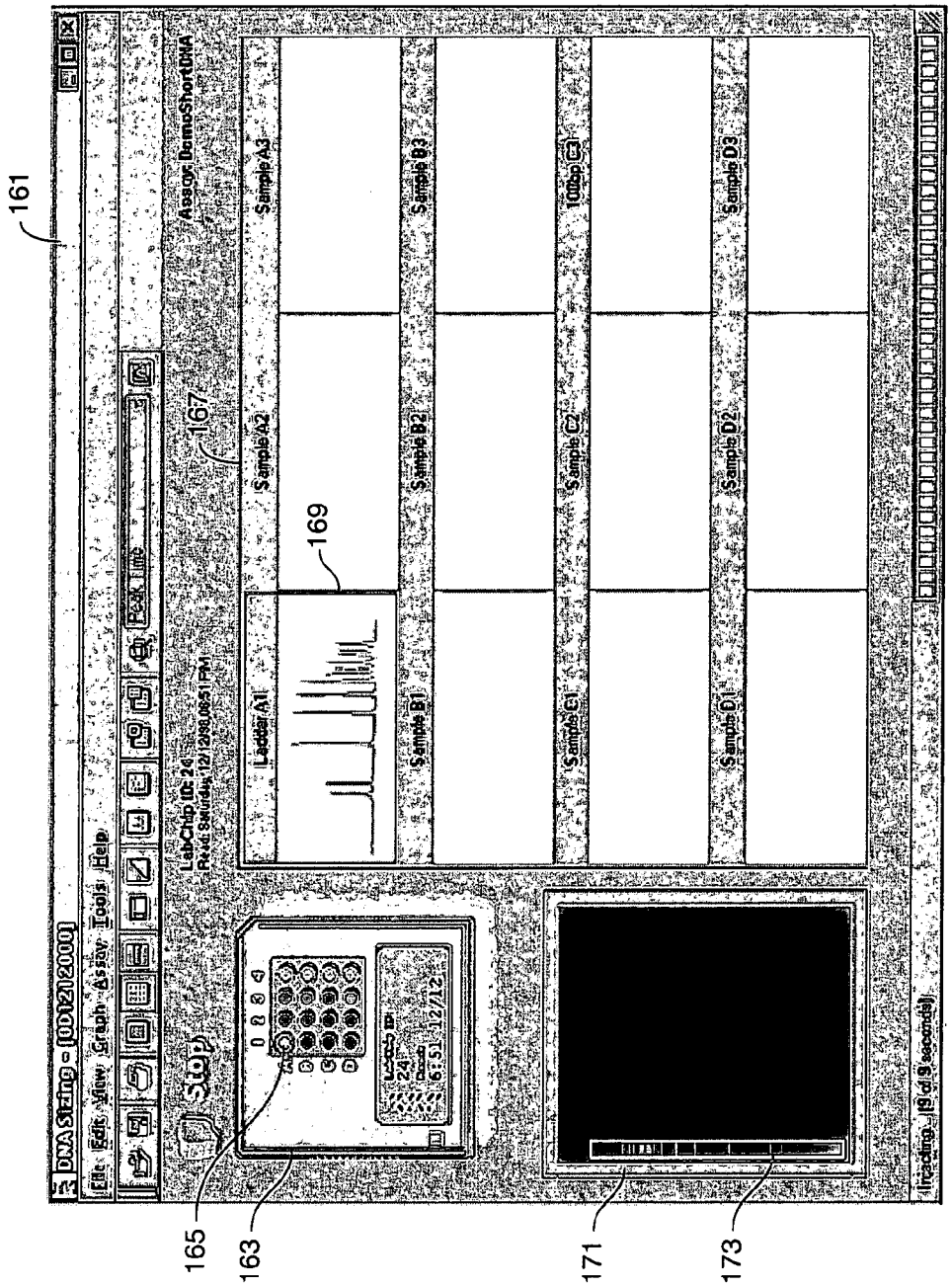
FIG. 6 shows a screen display of an embodiment of the invention including a series of bands.

FIG. 6 shows a screen display of an embodiment of the invention. A window 161 includes a graphical representation 163 of a microfluidic device (see FIG. 1). A circle 165 indicates the sample well that is currently selected or being processed. The graphical representation can also include other information including an identification number for the microfluidic device, the date and time the microfluidic device was read, and the like.

A window area 167 can show graphical plots of intensity vs. time for each of the sample wells that have been processed. Each plot is identified by the letter and number combination that uniquely identifies the row and column of the sample well (e.g., "A1" in this case). A graphical plot 169 shows the measured fluorescent intensity vs. time for the sample well identified as A1. The sample in well A1 is a ladder of a macromolecule, which in this example is a DNA ladder. If a sample designated by a user to include a ladder, the graphical plot is identified as a "Ladder" as shown, otherwise, the graphical plots are identified as "Sample."

A window area 171 includes a series of bands 173. The series of bands was generated from the series of measurements at a scanning location over time that produced graphical plot 169. However, series of bands 173 resembles the output from a conventional electrophoresis gel. As will be discussed in more detail below, window 161 includes many other innovative features.

In preferred embodiments, the samples (and ladders) include markers of known characteristics (e.g., molecular weight). The markers can be labeled with a distinctive marker such as fluorescent labels of a different wavelength or color so that they can be distinguished from constituents of the sample or they can be identified by other means (e.g., markers that are lighter or heavier than the expected constituents of a sample can be readily identified). The markers can be utilized to normalize the display of series of measurements as follows.

Figure 7:
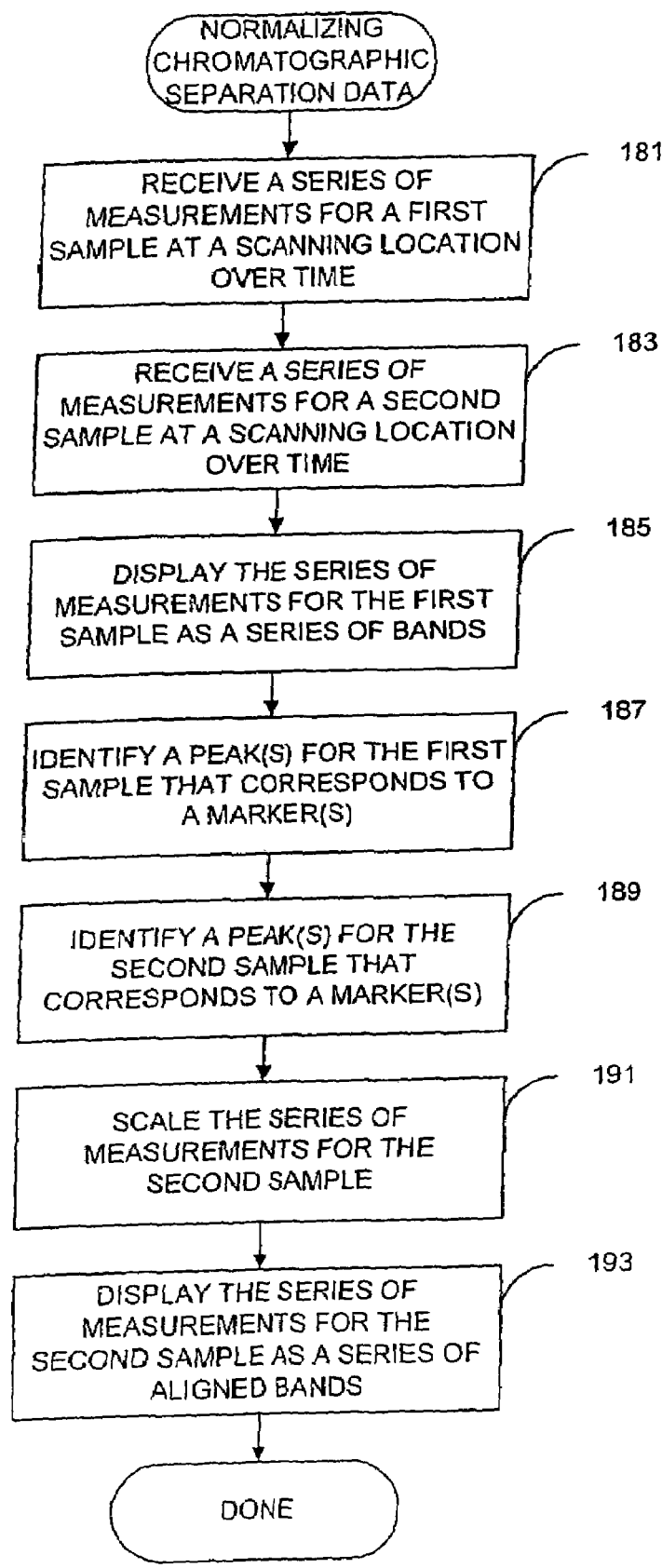
FIG. 7 shows a flowchart of a process of normalizing chromatographic separation data in which the samples include one or more markers.

FIG. 7 shows a flowchart of a process of normalizing chromatographic separation data in which the samples include one or more markers. Although the steps of the flowchart will be described in the order shown, no order of the steps should be necessarily implied. Steps of the flowcharts herein can be added, reordered, deleted, and combined without departing from the scope and spirit of the invention. For example, the data receiving steps are shown first as may occur when chromatographic separation data is read in from a storage device or network. However, if the data is processed in real-time, the data receiving steps may be interlaced in the other steps (see FIG. 9) so no order should be implied from the order in which the steps are shown.

At a step 181, the computer system receives a series of measurements for a first sample at a scanning location over time. The computer system receives a series of measurements for a second sample at a scanning location over time at a step 183. The series of measurements can be optionally displayed as a plot of intensity vs. time.

The computer system displays the series of measurements for the first sample as a series of bands at a step 185. As mentioned previously, the series of bands resembles a conventional electrophoresis gel. At a step 187, the computer system identifies one or more peaks in the series of measurements for the first sample that corresponds to a marker. In general, peaks in the series of measurements can indicate the presence of the labeled markers or constituents at the scanning location. At a step 189, the computer system identifies one or more peaks in the series of measurements for the second sample that corresponds to a marker. In a preferred embodiment, the peaks of markers are identified by a different wavelength that is exhibited by the labels on the markers as compared to the constituents.

At a step 191, the computer system scales the series of measurements for the second sample so that the marker or markers have the same measurement. For multiple markers, a linear stretch or compression using a point-to-point fit can be utilized. The computer system displays the series of measurements for the second sample as a series of bands that are aligned with and adjacent to the bands for the first sample at a step 193.

Figure 8A:
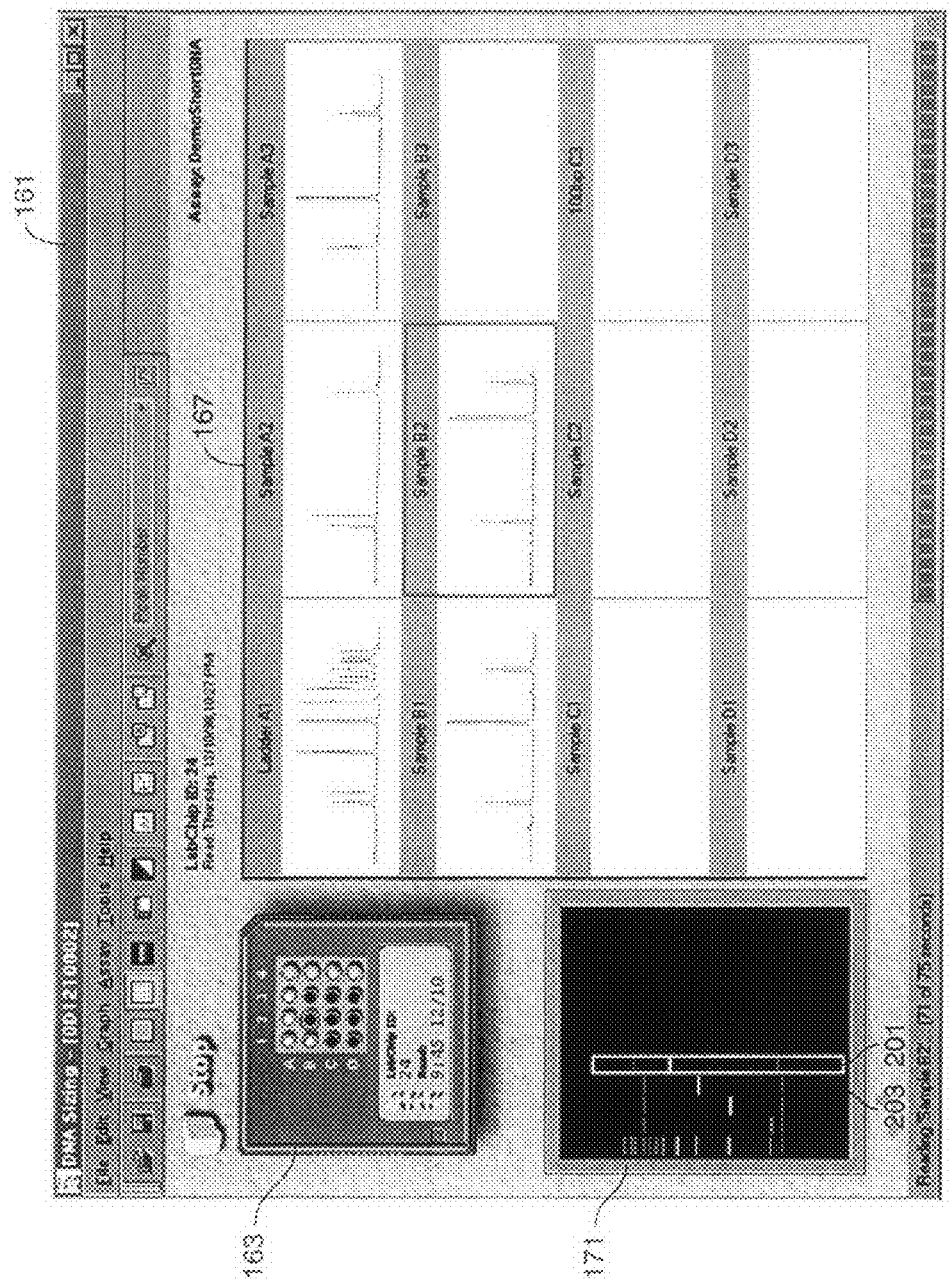
FIGS. 8A and 8B show screen displays that illustrate the normalizing process of series of bands.
Figure 8B:
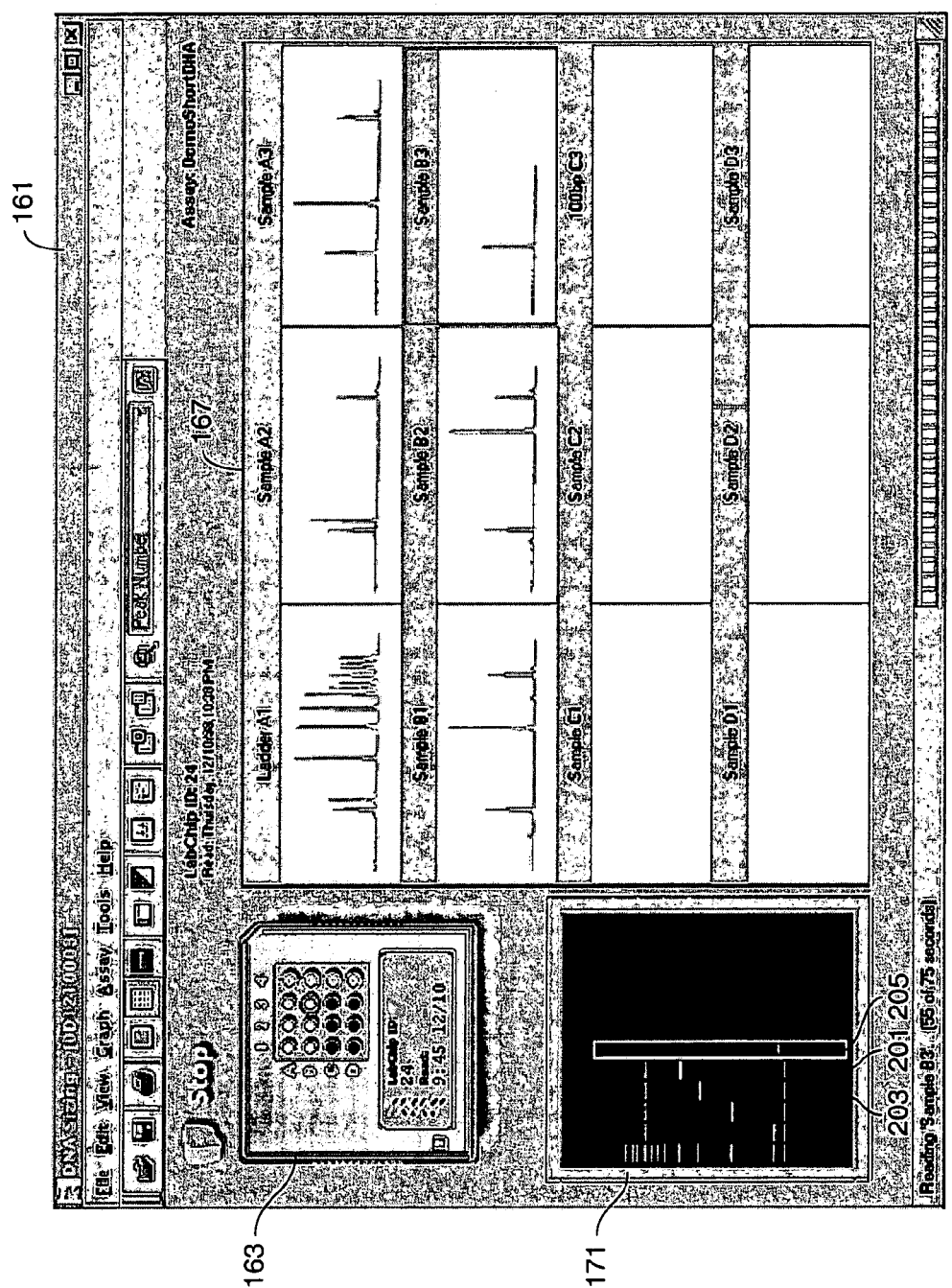

In order to illustrate the flowchart of FIG. 7, FIGS. 8A and 8B show screen displays that illustrate the normalizing process. In FIG. 8A, each sample is processed serially and as they are processed, the series of measurements are shown as graphical plots of intensities vs. time in window area 167 and a series of bands in a window area 171. As shown, sample B2 is being processed. A series of bands 201 is being displayed, where the top and bottom bands correspond to markers. In preferred embodiments, the bands that correspond to markers are displayed in a visually different manner (e.g., a different color) so the user can more readily identify the markers. However, it should be seen that series of bands 201 does not align with a series of bands 203 for sample B1 that was previously processed. As the series of bands are not aligned, it may be difficult to accurately compare the samples.

FIG. 8B shows the processing of the next sample, after the display of the data for sample B2 is normalized by the process shown in FIG. 7. As shown, series of bands 201 is now aligned with series of bands 203 (and all the previously processed samples). As sample B3 is being processed, it can be seen from a series of bands 205 that corresponds to the sample that it would also be beneficial to normalize series of bands 205.

Although FIGS. 8A and 8B show the series of bands being aligned to each other, the series of bands can also be aligned to predetermined locations on the screen. For example, a single marker in each sample can be utilized to align each displayed series of bands to a common baseline. Additionally, two markers in each sample can be utilized to align each displayed series of bands to a displayed scale.

Figure 9:
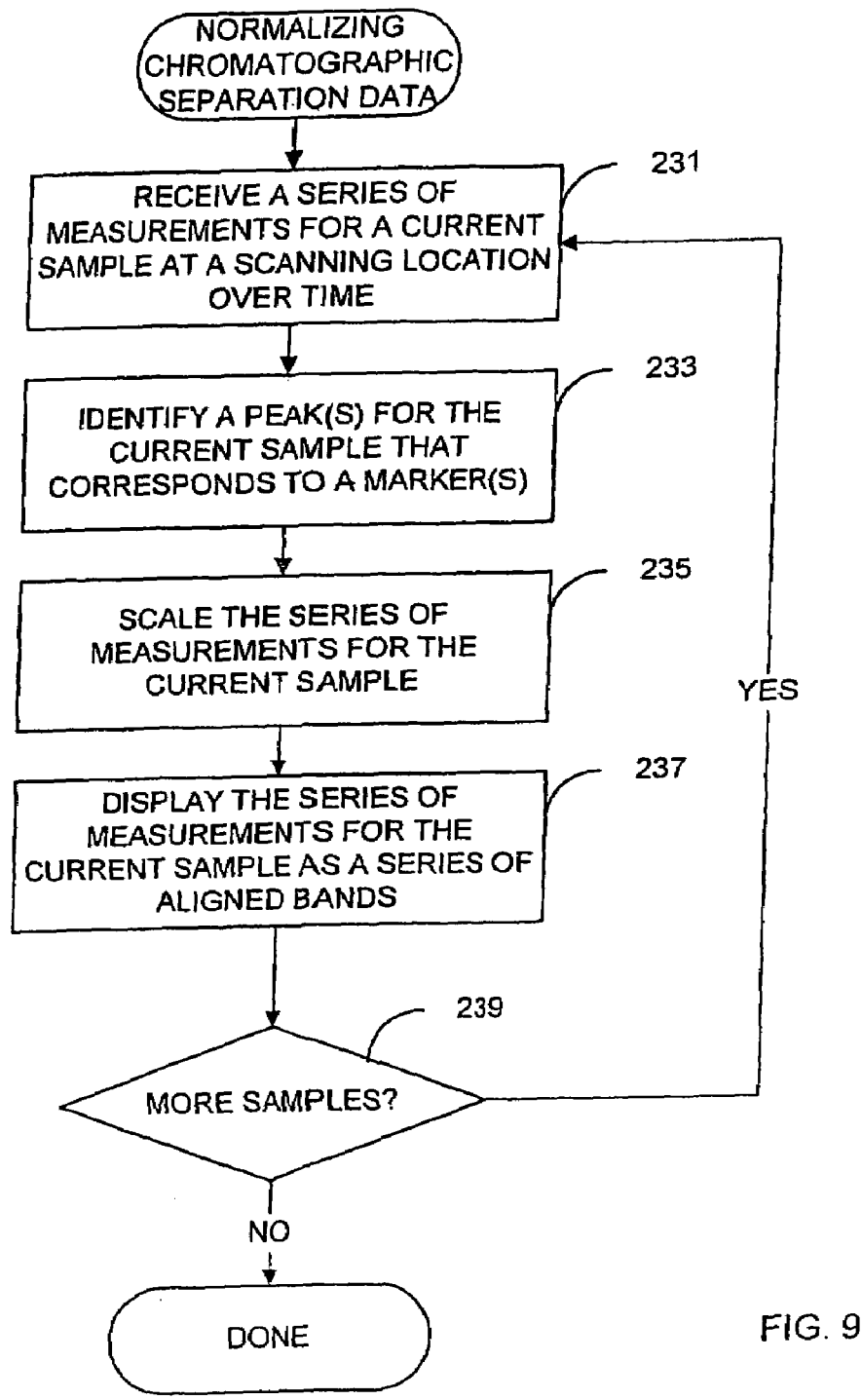
FIG. 9 shows a flowchart of another process of normalizing chromatographic separation data in which the samples include one or more markers.

FIG. 9 shows a flowchart of another process of normalizing chromatographic separation data in which the samples include one or more markers. In general, the flowchart serially processes each sample until all the samples have been processed. At a step 231, the computer system receives a series of measurements for a current sample at a scanning location over time. The series of measurements can be optionally displayed as a plot of intensity vs. time.

At a step 187, the computer system identifies one or more peaks in the series of measurements for the current sample that corresponds to a marker. The computer system scales the series of measurements for the current sample at a step 235. The series of measurements can be scaled so that the displayed bands that correspond to the marker or markers are aligned when displayed. Additionally, the series of measurements can be scaled to predetermined locations on the screen. The computer system displays the series of measurements for the current sample as a series of bands that are aligned with and adjacent to the bands for a previous sample (if any) at a step 237. If it is determined that there are more samples to process at a step 239, the flow returns to step 231.

Figure 10A:
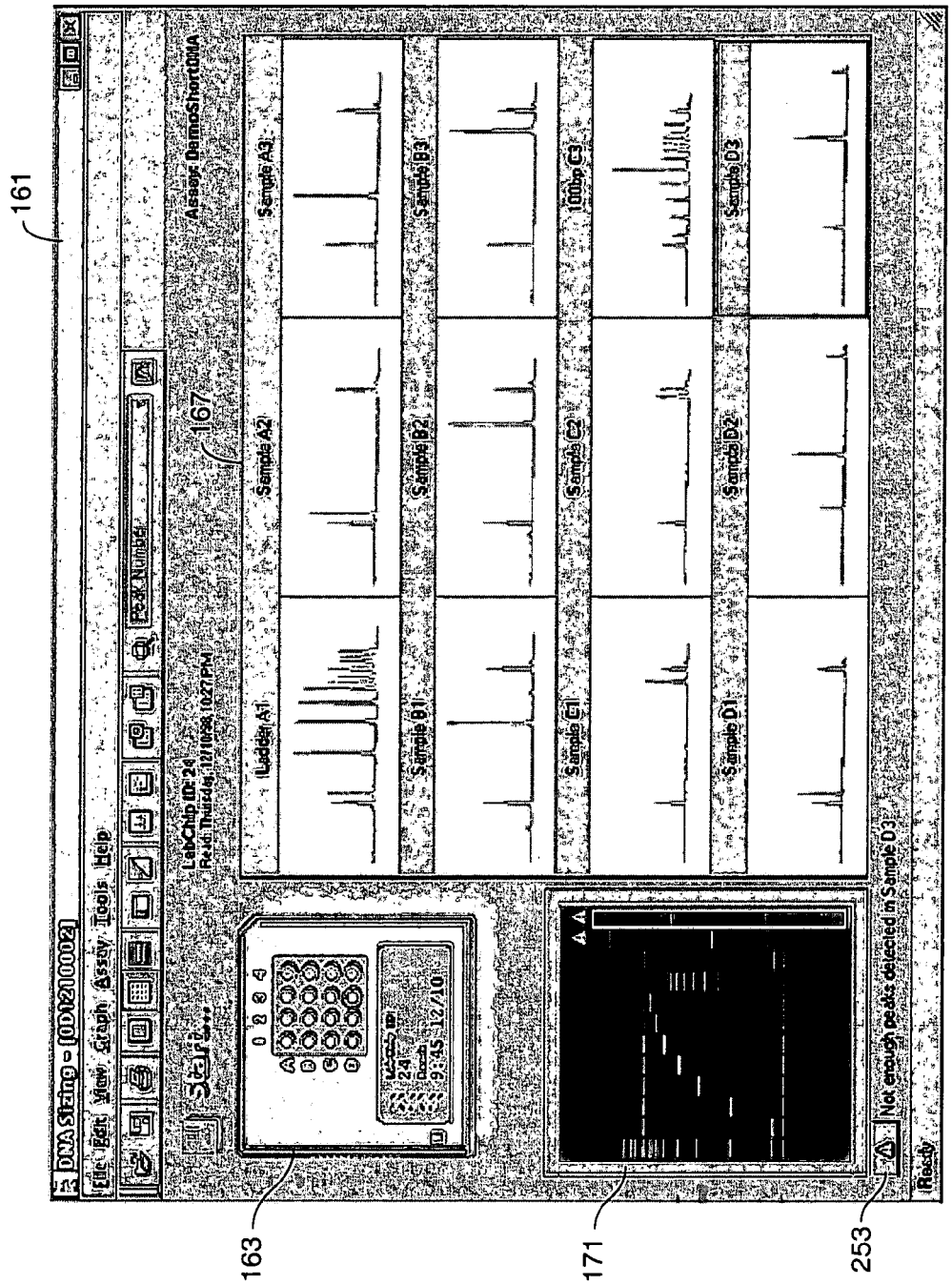
FIGS. 10A–10E show screen displays of embodiments of the invention.

FIGS. 10A–10E will illustrate some other innovative features of embodiments of the invention. FIG. 10A shows a screen display where all the sample wells have been processed. However, in processing two of the samples, it was determined that they did not have the requisite number of peaks (or the peaks did not satisfy certain criteria). Accordingly, series of bands 251 are shown with warning symbols that not enough peaks were detected. Additionally, a warning symbol 253 is displayed with a textual description of the warning since one of the samples with potentially bad data, sample D3, is currently selected.

Figure 10B:
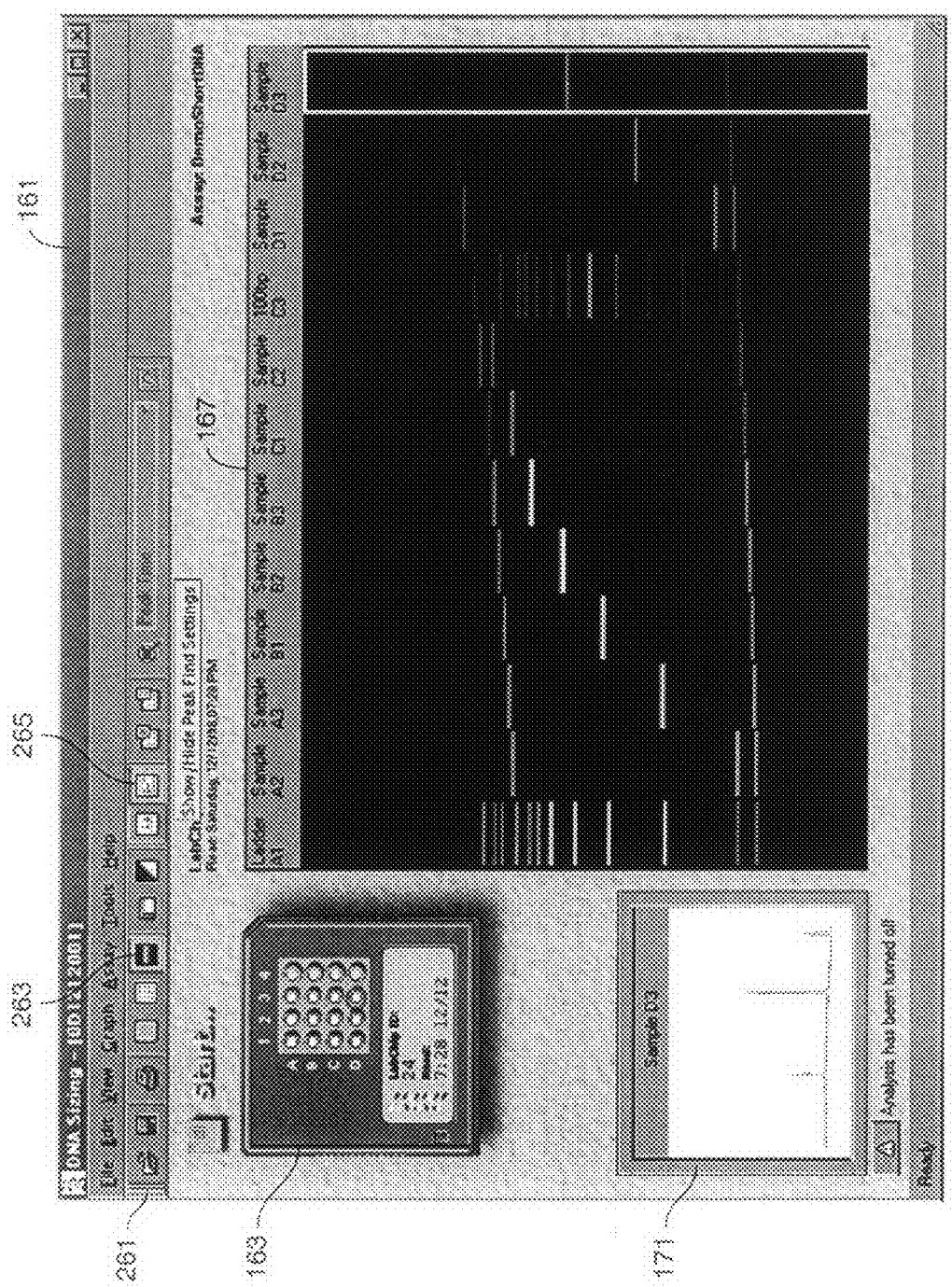

FIG. 10B shows a screen display in which the series of bands are shown in window area 167. Window 161 includes a toolbar 261. When a button 263 is activated, the series of bands are displayed in window area 167. Additionally, the graphical plot of intensity vs. time for the currently selected sample, sample D3, is displayed in window area 171. It may be observed that the series of bands in window area 167 are not normalized. A user can display the series of bands unaligned (i.e., as raw data) by activating a button 265.

Figure 10C:
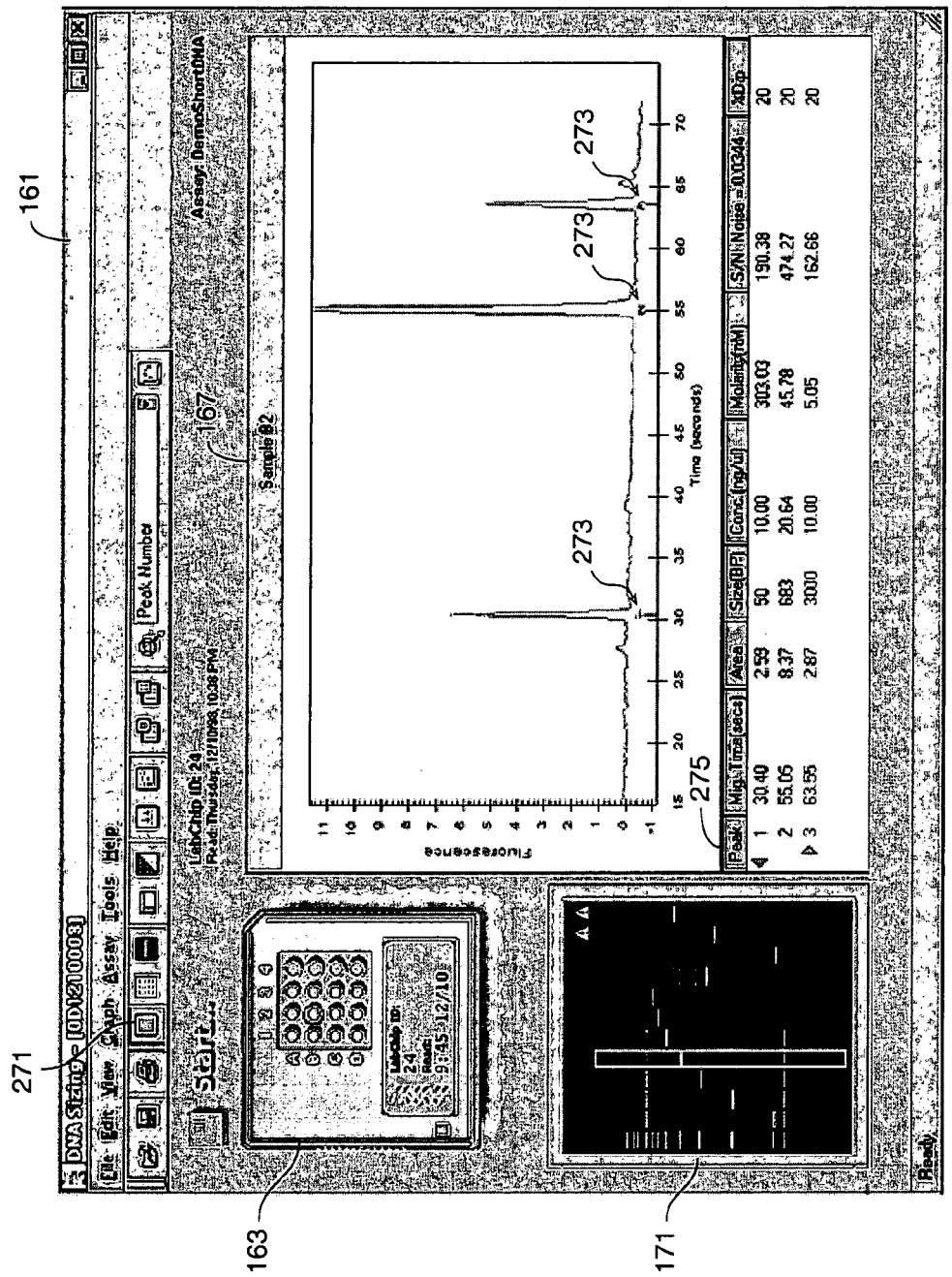

FIG. 10C shows a screen display where a single graphical plot is shown in window area 167. When a user activates a button 271, the graphical plot of the currently selected sample is enlarged and displayed alone in window area 167. Numbers 273 are utilized to identify each peak in window area 167. The window area includes a data table 275 that shows data for each of the numerically designated peaks. The data table shown includes the migration time, area of the peak, and a signal to noise ratio, which can be calculated by dividing the peak height by the well noise. Additionally, the size of the macromolecule represented by the peak (shown here in base pairs), concentration and molarity can be entered as properties of the assay and displayed in data table 275. Accordingly, the graphical plot of intensity vs. time can include the number of peaks and information regarding the data for each peak.

Figure 10D:
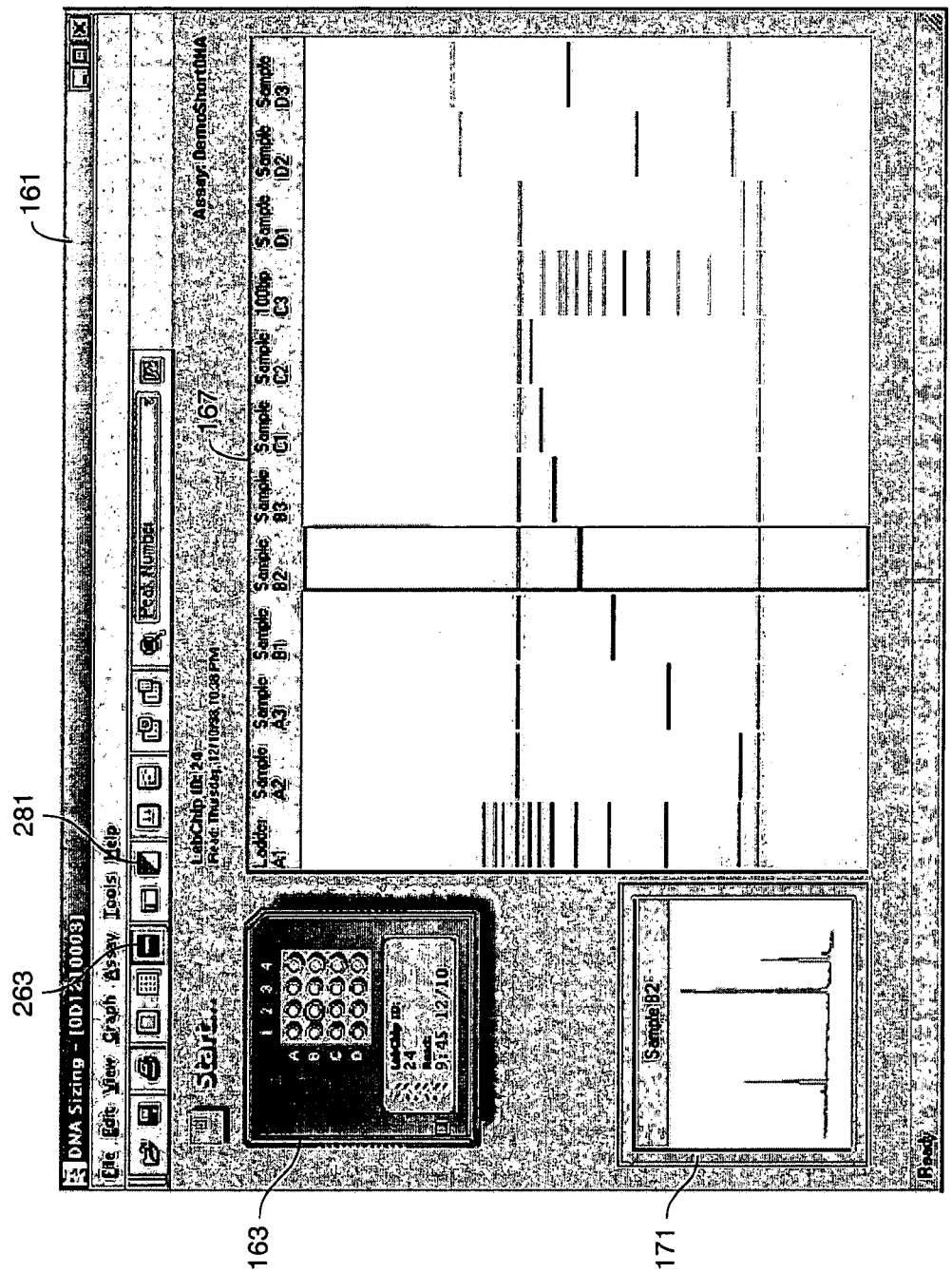

FIG. 10D shows a screen display where the display of the series of bands is inverted. Button 263 has been activated to display the series of bands in window area 167. As shown, the series of bands are normalized for easier comparison. A button 281 was activated that inverted the display of the series of bands. A user may prefer to see the series of bands inverted and activating button 281 will invert the display of the series of bands to their previous state.

Figure 10E:
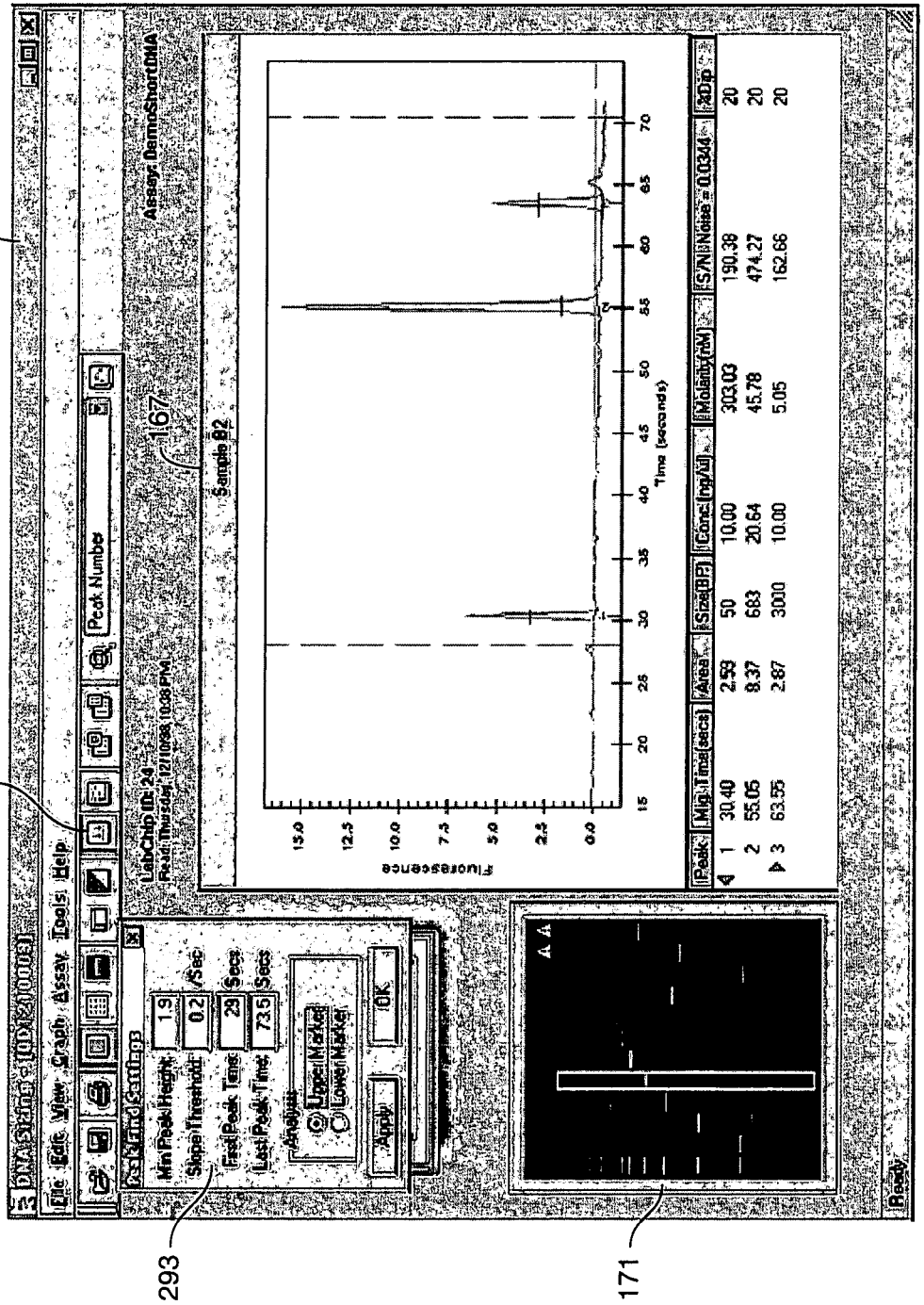

FIG. 10E shows a screen display where the user is able to modify the peak find settings. A button 291 can be activated to display the peak find settings so that the user may alter the way in which the data is analyzed. When button 291 is activated, a window 293 appears that shows the current peak find settings. The minimum peak height value determines whether or not a peak is kept. For each peak, the difference between the baseline and signal at the center point must be greater than the minimum peak height value. The slope threshold setting determines the difference in the slope that must occur in order for a peak to begin. The inverse of this value is used to determine the peak end.

The first and last peak time settings determine the window in which peaks will be found. Any peaks outside these settings will be rejected or ignored. The upper marker setting can be set to "nearest peak" or "last peak." The "last peak" setting refers to the last peak kept after the peak find algorithm is finished. The "nearest peak" setting refers to the peak that falls nearest the upper marker in the ladder from the first (or other specified) well. In preferred embodiments the "last peak" setting is the default.

Figure 11:
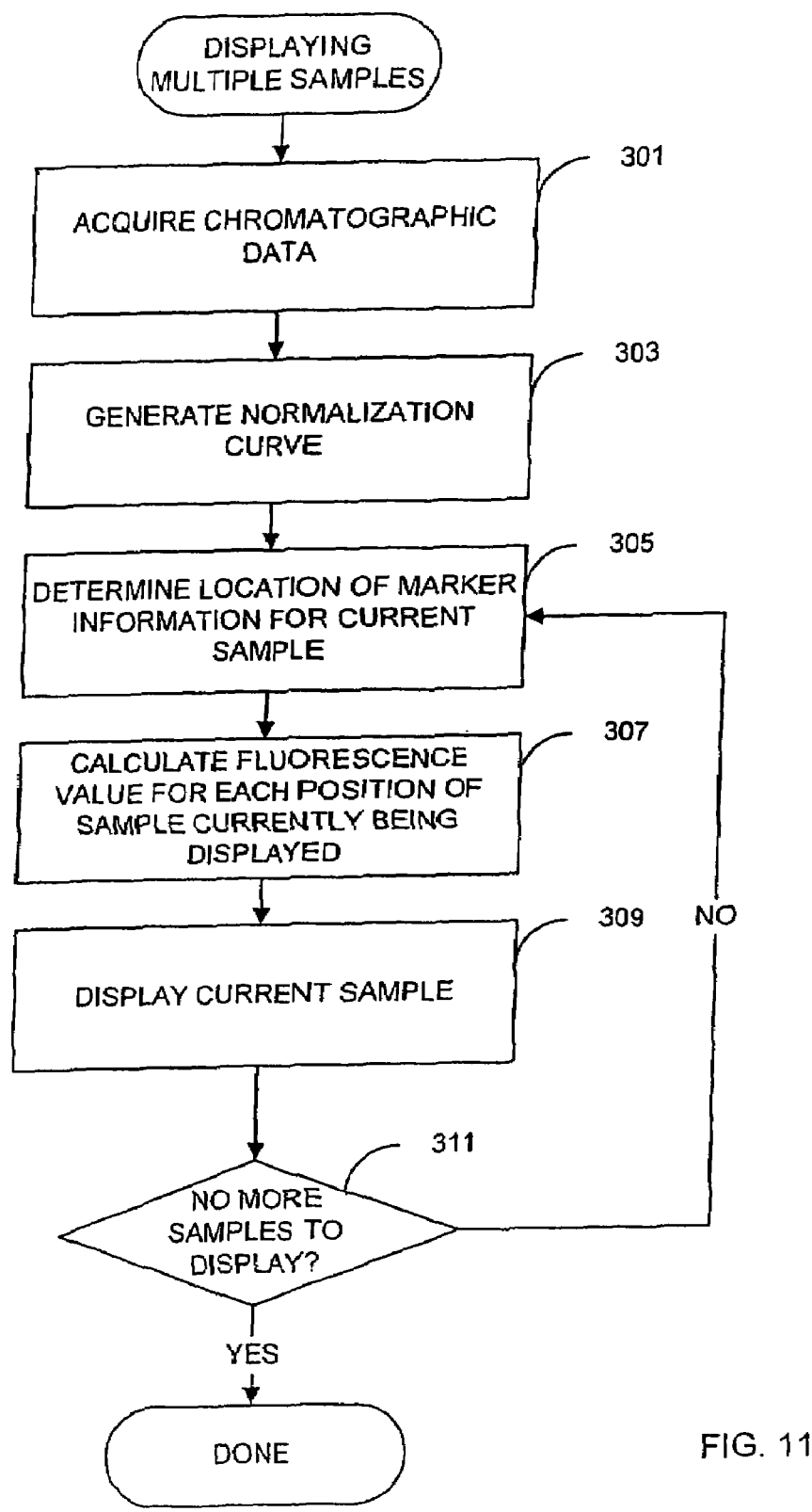
FIG. 11 shows a flowchart of a process of displaying chromatographic separation data for multiple samples.

FIG. 11 shows a flowchart of a process of displaying chromatographic separation data for multiple samples. As described above, the basic steps performed in the display of chromatographic information according to the present invention can begin by acquiring this information using a microfluidic instrument at a step 301. The output of the detection system is a signal that varies with the fluorescence of the material passing through the detector at the time. The present invention not only provides the ability to convert this serial stream of data into a more conventional format, but also to display the serially acquired data in a parallel format.

The standards introduced into the samples are preferably such that they are detected much earlier and much later than any of the constituents that might be expected to occur in the given sample, e.g., they have smaller and/or larger molecular weights. Such standards would thus be expected to occur before and after such constituents in a system such as that described above. Alternatively, internal standards may be used, such that the standards occur interspersed within the range of expected constituents.

In addition to acquiring chromatographic data for the samples being analyzed, chromatographic data can be acquired for a standard "ladder" of molecular species having known characteristics (e.g., molecular weight, charge, or other characteristic) over a given time period. This standard ladder can be used to generate a normalization curve, with the standards creating a curve that relates migration time to the known characteristic (e.g., molecular weight, charge, or the like) at a step 303. Using this information, each set of bands for each sample may be normalized such that the sample in each lane displayed may be properly compared to each of the other samples. This is done in the following manner.

At a step 305, the position of the markers in the given sample is determined. Next, fluorescence values are calculated for each position in the display of the sample currently being displayed at a step 307. It is at this point that the values of the unknown constituents are mapped to positions on the corresponding lane of the display. Thus, as mentioned above, the present invention converts the serial data into a more conventional parallel format. Normally, the sample data so displayed will then be normalized using the curve generated using the standard ladder. At a step 309, the results for the current sample are displayed. Finally, at a step 311, the process is repeated if more samples remain to be displayed.

Figure 12:
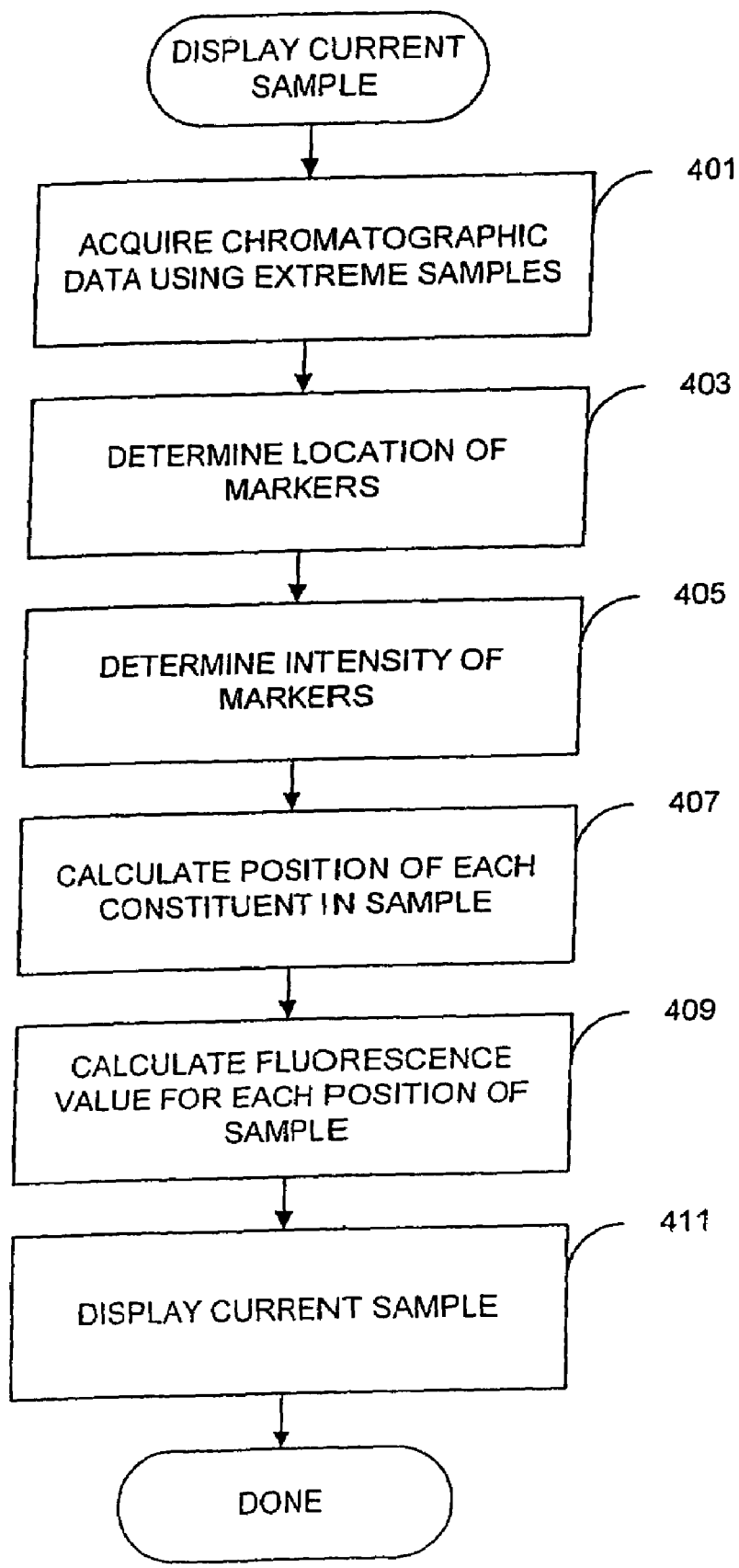
FIG. 12 illustrates in further detail a flowchart of a preferred process of generating a graphical display of chromatographic data for one sample.

FIG. 12 illustrates in further detail a flowchart of a preferred process of generating a graphical display of chromatographic data for one sample, according to the present invention. Again, the method begins by acquiring chromatographic data in some manner at a step 401. In this embodiment, standards having extreme molecular weights (relative to that of the sample's expected constituents) are introduced into the sample. The sample, along with the standards or markers therein, are run through the detection system. The smaller (i.e., lower molecular weight) fragments will normally be present at the output first (the smaller standard being presented before all others, ideally), followed by increasingly larger (i.e., greater molecular weight) fragments, followed at last by the larger of the two standards.

Next, at a step 403, the position of each of the standard markers is determined. This basically sets the range of possible values that will be displayed, assuming that none of the sample's constituents are larger or smaller than the standards employed. At a step 405, the intensity of the standard marker is determined so that the intensity of each band created by the sample's constituents may be scaled to a relative scale (arbitrary units are normally used in such a case).

At a step 407, the position of each of the constituents (as represented by one or more lines in the eventual displayed data) is scaled to the range determined in step 403. At a step 409, the intensity of each constituent is scaled to the arbitrary scaled just described. This information is then presented in a graphical format at a step 411.

Figure 13:
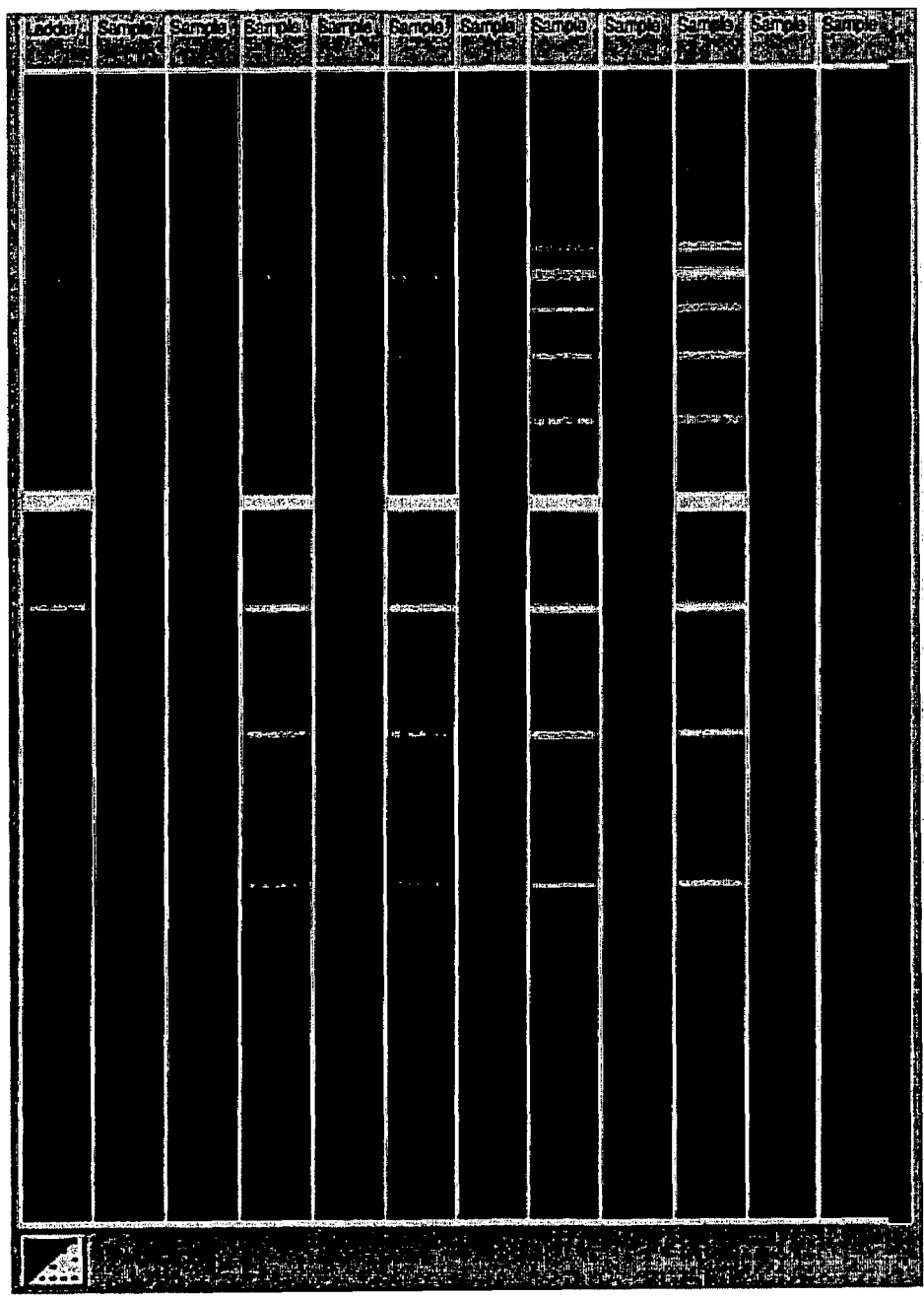
FIG. 13 depicts a gel display window according to one embodiment of the present invention.
Figure 14:
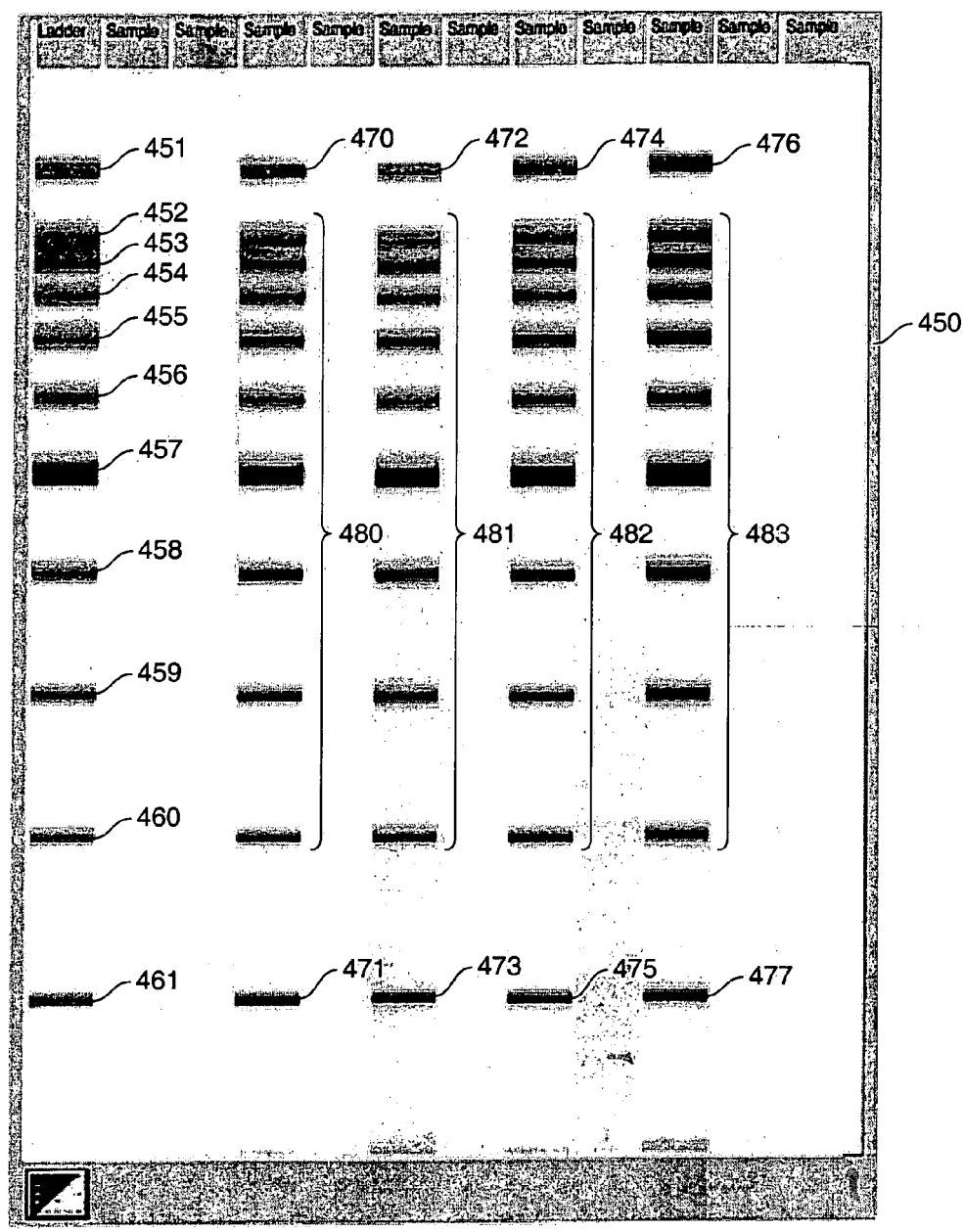
FIG. 14 depicts a gel display window according to another embodiment of the present invention.

FIGS. 13 and 14 illustrate a graphical display of chromatographic data (also referred to herein as a "gel display") according to one embodiment of the present invention. FIG. 13 illustrates a gel display using the more conventional light-on-dark color scheme reminiscent of agarose nucleic acid slab gels stained with fluorescent dyes. However, embodiments of the present invention are capable of displaying the given chromatographic data using any color scheme, allowing the user to adjust both foreground and background colors to improve the visibility of various features of the chromatographic data being displayed. Moreover, different bands (i.e., fragment sizes) may be displayed using different colors, allowing easy identification of the various constituents being displayed. In some embodiments, a user can change the contrast, brightness or perform "gamma" correction to facilitate viewing the gel display.

For reasons of clarity, the display illustrated in FIG. 14 will be described, although the following comments apply equally to FIG. 13. A standard ladder 400 and samples 410, 420, 430, and 440 are displayed in a gel display window 450 in FIG. 14. Standard ladder 400 contains numerous fragments of known size (i.e., standard-size fragments), which are displayed as bands 451–461. Sample ladders 410, 420, 430, and 440 also contain standard-size fragments corresponding to the fragments represented by bands 451 and 461. These are shown as bands 470, 472, 474, and 476, and bands 471, 473, 475, and 477, respectively. The samples' constituents are shown as sets of bands 480–483. As can be seen, samples 410, 420, 430, and 440 are substantially similar. This is evident because the position, width, and other characteristics of the bands in each of sets of bands 480–483 are substantially similar.

As can be seen, the present invention matches the smallest and largest standard fragments in each of sample ladders 410, 420, 430, and 440 to those in standard ladder 400 (i.e., bands 451 and 461). The display is calibrated using bands 452–460 of standard ladder 400. Thus, the size and position of one or more bands in sets of bands 480–483 may then be determined by determining the given band's position using, for example, a "rollover" feature. This feature allows a selected position on the interpolation curve or on a lane of the gel display to be identified using the screen cursor. This position may then be related to a given molecular weight, fragment length, or other criteria of the constituents of the samples being analyzed. In this manner, the user can obtain instantaneous display of the characteristic (molecular weight, fragment length, or the like) by simply placing the cursor over the band of interest. Alternatively, each band can be automatically identified, and a fragment size displayed by the band in question.

The present invention offers several advantages. For example, once the chromatographic data has been analyzed and converted into a gel format, several advantageous features may be provided. A major advantage of the present invention is the invention's ability to display data collected serially in a more conventional format. Moreover, the present invention permits a single standard ladder to be analyzed once for any number of runs, using the preferred chromatographic data collection system, for example. In the prior art, a standard ladder must be run for each gel, because gel characteristics vary from gel to gel. Thus, a lane is used in each and every gel that is run. In a preferred embodiment of the present invention, because there would be no substantial difference from run to run, only a single ladder would need to be run, saving time and lowering operating expenses.

In a further advantage, the data in the gel format is digitized, making its display very flexible compared to conventional gels. For example, when displaying the analog of a protein gel, the gel display may use a light coloring on a dark background to emulate a silver halide process (normal contrast, as shown in FIG. 13), or a dark coloring on a light background to emulate a lithium bromide process (reverse contrast, as shown in FIG. 14). Further, the digitized gel is easily stored, printed, and reproduced from its digitized format.

Another advantage is the ability to automatically align the various constituents represented in two or more samples to markers included in the samples. This may be necessary if the raw data from various samples does not match up properly, or is skewed for some reason (e.g., varied separation conditions). For example, if two samples are to be compared, but the samples differ in the ranges of molecular weights of the constituents therein (or fail to match up for some other reason), their markers may be matched/aligned. Thus, one or both of the samples' gel representations are translated from their current state to a translated state in which each point is mapped from its current position to a new position. When this process is completed, each marker in the first sample should substantially match each marker in the second sample. This process is referred to herein as warping. Internal markers may be used in such a situation to further improve the accuracy of such warping. This warping allows for a display according to the present invention to account for non-linearities that may vary from sample to sample, when displaying such samples for comparison.

Finally, the graphical display of the present invention allows systems that generate data in a serial fashion to display and compare such data in parallel. In other words, for a system that records fluorescence data for each sample on after the other, the present invention allows the viewing of such data as a parallel set of lanes. This is similar to a traditional gel, in which multiple lanes are generated. However, unlike the traditional gel, the present invention is not forced to display the data in this manner. In a traditional gel, the number of lanes used should be maximized because the gel cannot be reused. Because a processing system that generates data serially runs analyses one at a time and the present invention stores and displays that information at a later time, no such limitations are imposed. Thus, the present invention may display the chromatographic separation data singly, in pairs, or in any other configuration that the user finds advantageous.

The invention has now been explained with reference to specific embodiments. Other embodiments will be apparent to those of ordinary skill in the art in view of the foregoing description. For example, the invention can be advantageously applied to other microfluidic devices and various types of molecules in addition to those described herein. It is therefore not intended that this invention be limited except as indicated by the appended claims along with their full scope of equivalents.

What is claimed is:

1. A system comprising:
   a microfluidic device on which a sample is subjected to a chromatographic separation process;
   a microfluidic instrument comprising a detection system that detects results of the chromatographic separation process; and
   a computer system that receives chromatographic separation data corresponding to the results from the microfluidic instrument, wherein the computer system comprises
      a processor, and
      a computer readable medium coupled to the processor that stores a computer program that presents the chromatographic separation data from the sample as a series of bands;
   wherein the computer presents a first set of bands from chromatographic separation data from a first sample adjacent to a second set of bands from chromatographic separation data from a second sample; and
   wherein the computer program also identifies a band in the first set of bands that corresponds to a marker in the first sample, identifies a band in the second set of bands that corresponds to the same marker in the second sample, and aligns the bands when presenting the two sets of bands adjacent to each other.

2. The system of claim 1, wherein the microfluidic device comprises two intersecting channels.

3. The system of claim 2, wherein the two intersecting channels meet at a cross intersection.

4. The system of claim 1, wherein the microfluidic device comprises a substrate layer made of a silica based material.

5. The system of claim 1, wherein the microfluidic device comprises a substrate layer made of a polymeric material.

6. The system of claim 1, wherein the microfluidic instrument further comprises an electrokinetic based flow system.

7. The system of claim 1, wherein the microfluidic instrument further comprises a pressure based flow system.

8. The system of claim 1, wherein the detection system comprises an optical detection system.

* * * * *